United States Patent
Ing et al.

(10) Patent No.: US 11,989,629 B2
(45) Date of Patent: *May 21, 2024

(54) SYSTEMS AND METHODS FOR PREDICTING ANALYTE CONCENTRATIONS VIA MACHINE LEARNING TECHNIQUES

(71) Applicant: Metre, Inc., Oakland, CA (US)

(72) Inventors: Nicole Leilani Ing, Emeryville, CA (US); Glenn Clifford Forrester, Oakland, CA (US)

(73) Assignee: Metre, Inc., Oakland, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/355,157

(22) Filed: Jun. 22, 2021

(65) Prior Publication Data

US 2022/0114485 A1     Apr. 14, 2022

Related U.S. Application Data

(63) Continuation of application No. 17/067,573, filed on Oct. 9, 2020, now Pat. No. 11,068,803.

(51) Int. Cl.
*G06N 20/00*     (2019.01)
*G01N 27/49*     (2006.01)
*G01N 33/497*    (2006.01)

(52) U.S. Cl.
CPC ............ *G06N 20/00* (2019.01); *G01N 27/49* (2013.01); *G01N 33/497* (2013.01)

(58) Field of Classification Search
CPC .......... G06N 20/00; G06N 3/08; G01N 27/49; G01N 33/497; A61B 5/082; A61B 5/0836; A61B 5/087; A61B 5/097
See application file for complete search history.

(56) References Cited

U.S. PATENT DOCUMENTS

| | | | |
|---|---|---|---|
| 11,172,845 B1 * | 11/2021 | Everman | G01N 33/497 |
| 2016/0245797 A1 | 8/2016 | Ahmad et al. | |
| 2018/0146888 A1 | 5/2018 | Guntner et al. | |
| 2019/0125211 A1 | 5/2019 | Reddy et al. | |

(Continued)

FOREIGN PATENT DOCUMENTS

WO     2020/186335 A1     9/2020

OTHER PUBLICATIONS

International Search Report in PCT International Application No. PCT/US2021/053837, dated Jan. 10, 2022.

(Continued)

*Primary Examiner* — James J Yang
(74) *Attorney, Agent, or Firm* — Cognition IP, P.C.; Edward Steakley; Rajesh Fotedar

(57) ABSTRACT

Various embodiments of an apparatus, methods, systems and computer program products described herein are directed to a Concentration Prediction Platform. According to various embodiments, the Concentration Prediction Platform receives an electrochemical signal and generates data based on deconvolving a respective contribution of an analyte(s) influencing the electrochemical signal. The Concentration Prediction Platform sends the data into one or more machine learning networks. The Concentration Prediction Platform receives, from the one or more machine learning networks, a predicted concentration of an analyte(s) influencing the electrochemical signal.

20 Claims, 8 Drawing Sheets

System Diagram

(56) References Cited

U.S. PATENT DOCUMENTS

| | | |
|---|---|---|
| 2020/0015708 A1 | 1/2020 | Uplinger |
| 2020/0072808 A1* | 3/2020 | Dhurandhar ............ G16C 20/70 |
| 2020/0124625 A1 | 4/2020 | Dunlop et al. |
| 2020/0170545 A1 | 6/2020 | Reddy |
| 2020/0229735 A1* | 7/2020 | Muchmore .......... A61B 5/7225 |
| 2020/0268278 A1 | 8/2020 | Ratto et al. |
| 2020/0337594 A1 | 10/2020 | Reddy |
| 2021/0190360 A1* | 6/2021 | Lee .......................... F24F 11/58 |

* cited by examiner

400

402 — Receive sensor data associated with exhaled breath

404 — Utilize at least a portion of the sensor data as input to a machine learning network 406 — Receive output from the machine learning network based in part on a concentration of acetone and a concentration carbon dioxide present in the exhaled breath

404
Utilize at least a portion of the sensor data as input to a machine learning network 502
Implementing a machine learning network trained according to a cross-point observation 504
Defining the cross-point observation at least in part as an intersection of a first acetone response curve and a second acetone response curve

CROSS-POINT = SAME INTERSECTION POINT

First acetone response curve for (acetone 1, temp 1, co 1)

Second acetone response curve for (acetone 1, temp 1, co 2)

Third acetone response curve for (acetone 1, temp 1, co 3)

⋮

$N$ th acetone response curve for (acetone 1, temp 1, co $N$)

FIG. 5

SYSTEMS AND METHODS FOR PREDICTING ANALYTE CONCENTRATIONS VIA MACHINE LEARNING TECHNIQUES

CROSS-REFERENCE TO RELATED APPLICATIONS

This application is a continuation of U.S. application Ser. No. 17/067,573, filed Oct. 9, 2020, which is hereby incorporated by reference in its entirety.

BACKGROUND

In the field of computer science, artificial intelligence ("AI") networks, such as neural networks and deep learning networks, are increasingly being employed to solve a variety of tasks and challenging problems. Such AI networks can consist of layers of computational graphs with nodes representing computational operations and connections in between those operations and/or computational graphs with filters representing the extraction of features from input data. Each operation computes or extracts something from the input data and/or previous layer in order to produce output data and/or next layer. Within AI networks there are fairly predefined operations, and there can be, e.g., hundreds or thousands of these operations. Such operations can represent such computational tasks as matrix multiplication and convolution, often using many pieces of input data from within the network.

SUMMARY

Various embodiments of an apparatus, methods, systems and computer program products described herein are directed to a Concentration Prediction Platform. Various embodiments of the Concentration Prediction Platform are directed to deconvolving the contribution of two or more analytes to an electrochemical signal by training a machine learning algorithm(s) on the major constituents that influence the electrochemical signal, such as, for example: concentration and temperature. The Concentration Prediction Platform implements nonets and contrastive/triplet loss to teach the nonets the following constituents: 1) comparing how the signal is affected by different concentrations of a single analyte in the presence of a second analyte, 2) comparing how the signal is affected by different concentrations of the second analyte in the presence of the first analyte, 3) comparing the effects of different temperatures on the first constituents ("1"), 4) comparing the effects of different temperatures on the second constituents ("2"), and 5) comparing the effects of different temperatures on the signal in general.

The various embodiments described herein provide improvements and advantages over conventional systems by, for example, implementing an electro-chemical cell(s) and machine learning techniques to predict and/or deliver accurate measurements of acetone concentration and carbon dioxide concentration related to one or more sample(s) of exhaled breath. According to various embodiments, the Concentration Prediction Platform receives an electrochemical signal and generates data based on deconvolving a respective contribution of two or more analytes influencing the electrochemical signal. The Concentration Prediction Platform sends the data into one or more machine learning networks. The Concentration Prediction Platform receives, from the one or more machine learning networks, a predicted concentration of at least one of the analytes influencing the electrochemical signal. The one or more machine learning networks are trained via the Concentration Prediction Platform according to a plurality of input nonets to learn contrastive triplet loss from one or more sets of nonet comparisons. According to various embodiments, the Concentration Prediction Platform may also train the machine learning network(s) as described herein to detect one or more volatile organics and not solely acetone concentrations and/or carbon dioxide concentrations. For example, the Concentration Prediction Platform may be directed to training the machine learning network(s) on and detecting concentrations of ethanol, isopropanol, methanol, methane, hydrogen, and/or acetaldehyde. The Concentration Prediction Platform may be directed to training the machine learning network(s) on and detecting concentrations of any other type of substance.

According to various embodiments, the Concentration Prediction Platform measures a concentration of one or more constituents of a fixed volume gas sample applied to a sensor(s). The Concentration Prediction Platform receives sensor data and utilizes at least a portion of the sensor data as input to a machine learning network. The Concentration Prediction Platform receives output from the machine learning network based in part on a concentration of a substance. According to various embodiments, the Concentration Prediction Platform receives sensor data associated with exhaled breath and utilizes at least a portion of the sensor data as input to a machine learning network. The Concentration Prediction Platform receives output from the machine learning network based at least in part on a concentration of acetone and a concentration carbon dioxide present in the exhaled breath. In various embodiments, output from Concentration Prediction Platform may be a determined level of ketones in an individual's blood based on a sample of exhaled breath of that same individual. It is understood that various embodiments described herein are not limited to a signal(s) associated with a sample(s) of exhaled breath.

According to various embodiments, the Concentration Prediction Platform may include a machine learning network and be in communication with a sensor, such as an electro-chemical fuel cell(s). The sensor may be exposed to a sample of exhaled breath captured by a breathalyzer component and the sensor may generate a voltage that corresponds to the sample. In various embodiments, the sensor may be a component within the breathalyzer component. Time series data associated with the voltage may be generated. The Concentration Prediction Platform may receive the time series data at a cloud-based platform that interacts with the machine learning network. In other embodiments, the time series data may be generated by the Concentration Prediction Platform at the cloud-based platform. According to various embodiments, the machine learning network may be implemented to reflect a crosspoint observation.

According to various embodiments, the Concentration Prediction Platform determines a status of the electrochemical cell via the machine learning network and receives output identifying one or more algorithms to be applied to the electro-chemical cell to modify the status of the electrochemical cell. In some embodiments, the machine learning network may be implemented on the electro-chemical cell and/or across a plurality of electro-chemical cells.

According to various embodiments, the Concentration Prediction Platform may receive a signal associated with a sample(s) that contains, at least in part: ethanol, isopropanol, methanol, methane, hydrogen and/or acetaldehyde. For example, various embodiments may be directed to a concentration(s) of ethanol, isopropanol, methanol, methane, hydrogen or acetaldehyde instead of an acetone concentration(s) of the embodiments described herein.

According to various embodiments, the Concentration Prediction Platform may train the machine learning network by analyzing at least a subset of training data and generating additional training data based on the subset of training data. For example, the additional training data may include triplet values for temperature, acetone concentration and carbon dioxide concentration based on cross-point relationships observed between values of temperature, acetone concentration and carbon dioxide concentration triplets present in the subset of training data. Training the machine learning network may be based on input training nonets, where each training nonet represents data from nine different tests performed (and/or simulated) with regard to the same sensor. According to various embodiments, a training nonet may correspond to different tests on the same sensor with regard to different samples.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 4 is a diagram illustrating an exemplary method that may be performed in some embodiments may operate.

FIG. 5 is a diagram illustrating an exemplary environment in which some embodiments may operate.

DETAILED DESCRIPTION

Figure 1A:
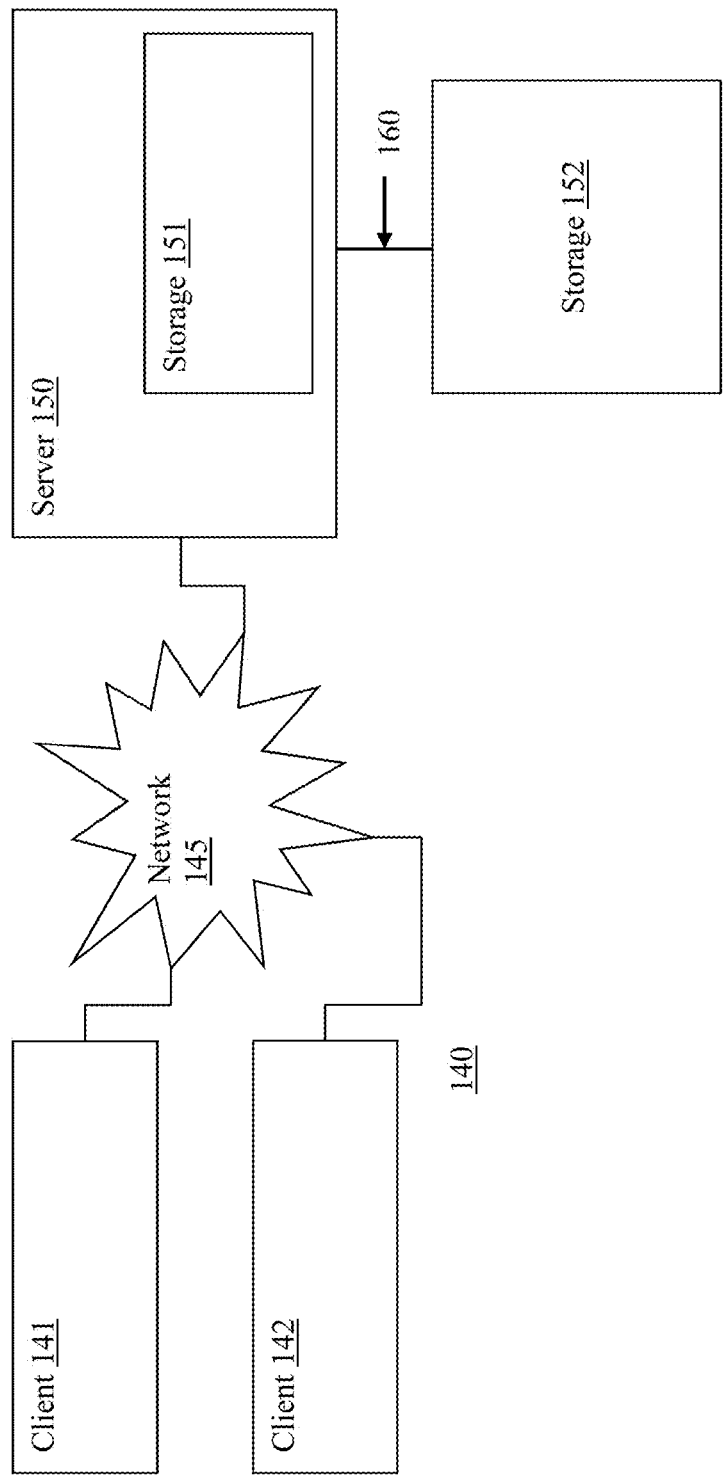
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients. Server 150 may be implemented as a number of networked server devices, though it is illustrated as a single entity. Communications and transmissions between a base station and one or vehicles and between a base station and one or more control centers as described herein may be executed similarly as the client 141, 142 requests.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151.

In another embodiment, the client 141 may be a vehicle that sends vehicle sensor data used during execution of the method 200 or other method herein. This may be accomplished via communication over the network 145 between the client 141 and server 150. For example, the client may communicate a request to the server 150 to store a file with a specified file name in the storage 151. The server 150 may respond to the request and store the file with the specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
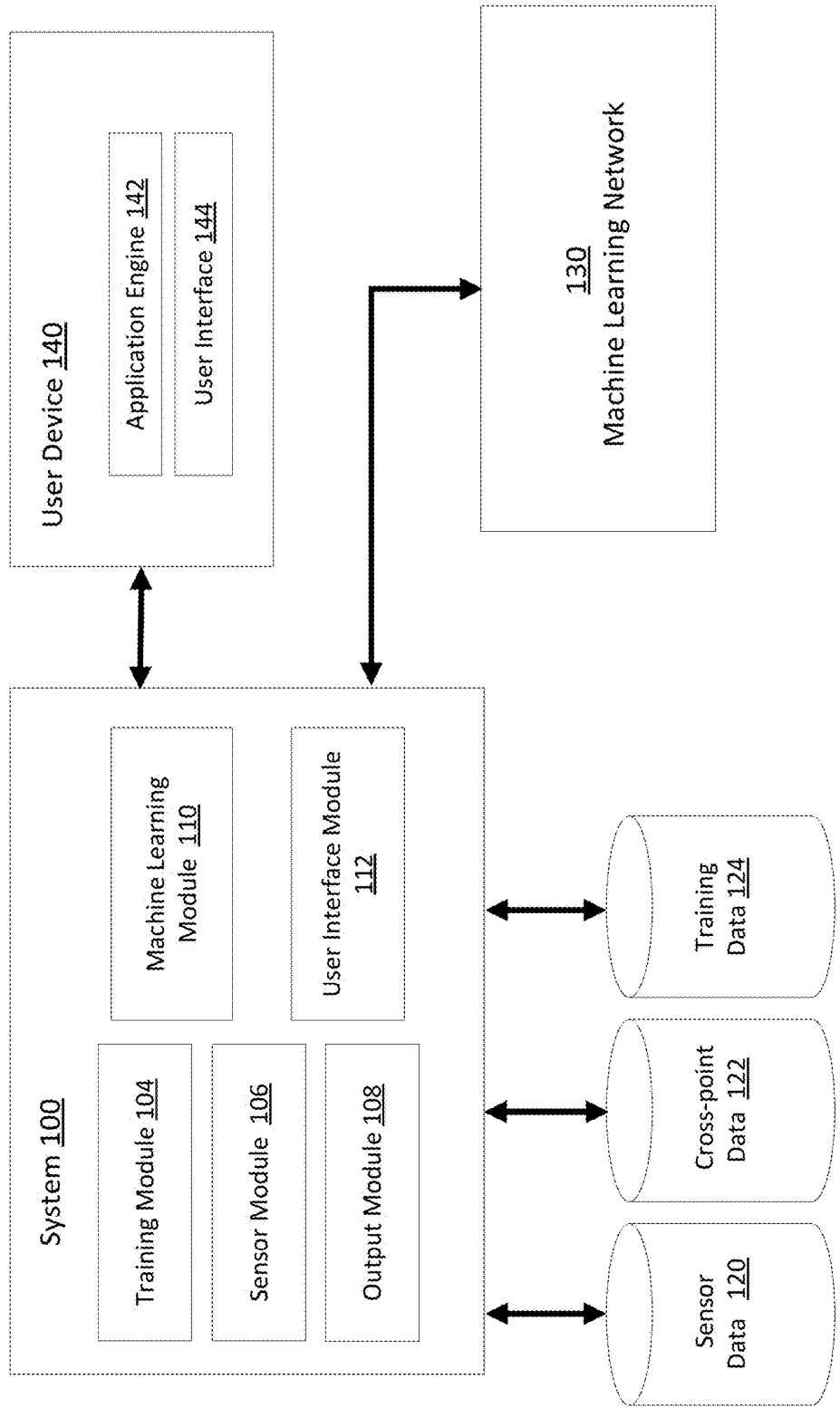
FIG. 1B is a diagram illustrating an exemplary environment in which some embodiments may operate.

FIG. 1B illustrates a block diagram of an example system 100 for a Concentration Prediction Platform that includes a training module 104, a sensor module 106, an output module 108, a machine learning module 110 and a user interface (U.I.) module 112. The system 100 may communicate with a user device 140 to display output, via a user interface 144 generated by an application engine 142.

Figure 3:
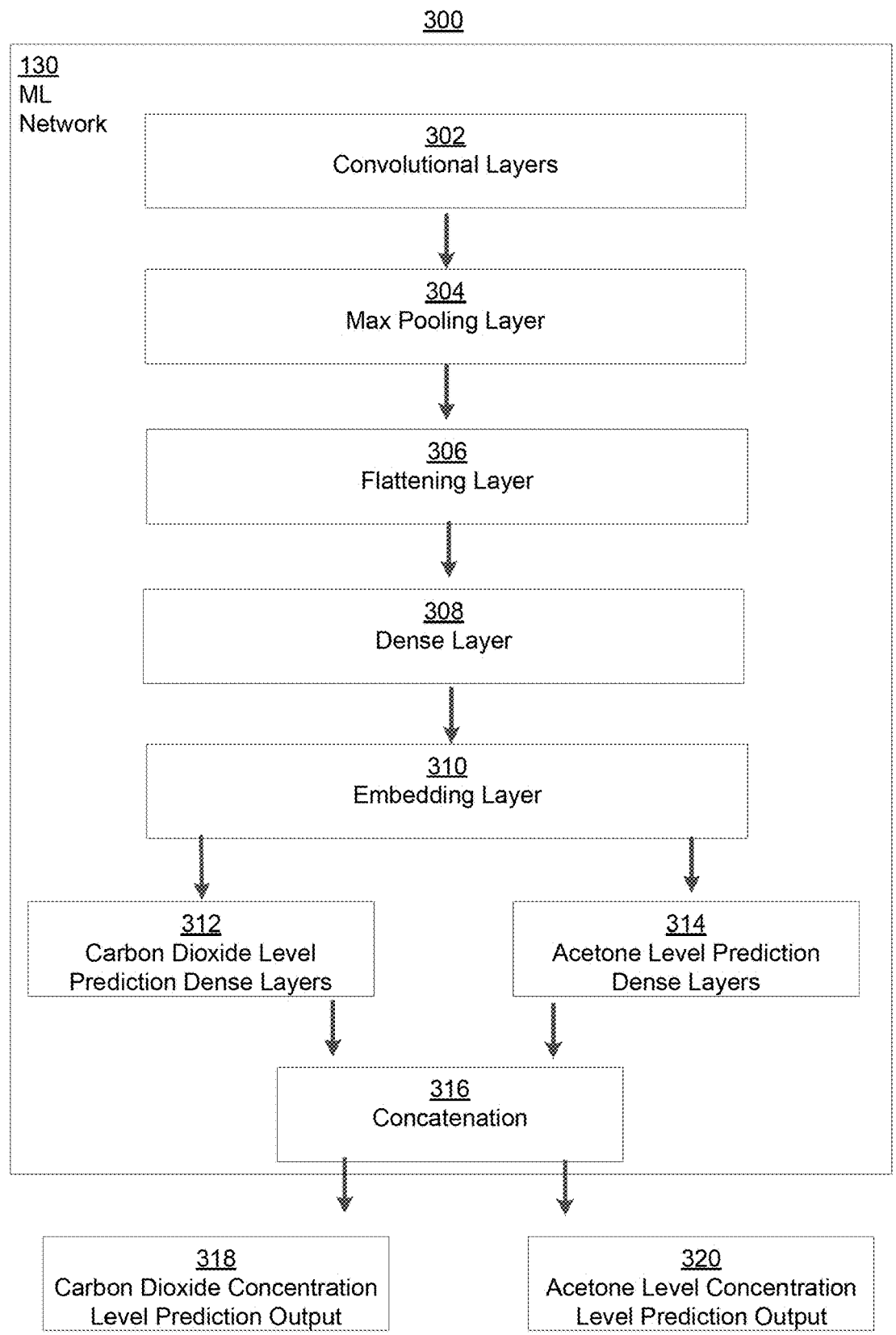
FIG. 3 is a diagram illustrating an exemplary environment in which some embodiments may operate.
Figure 6:
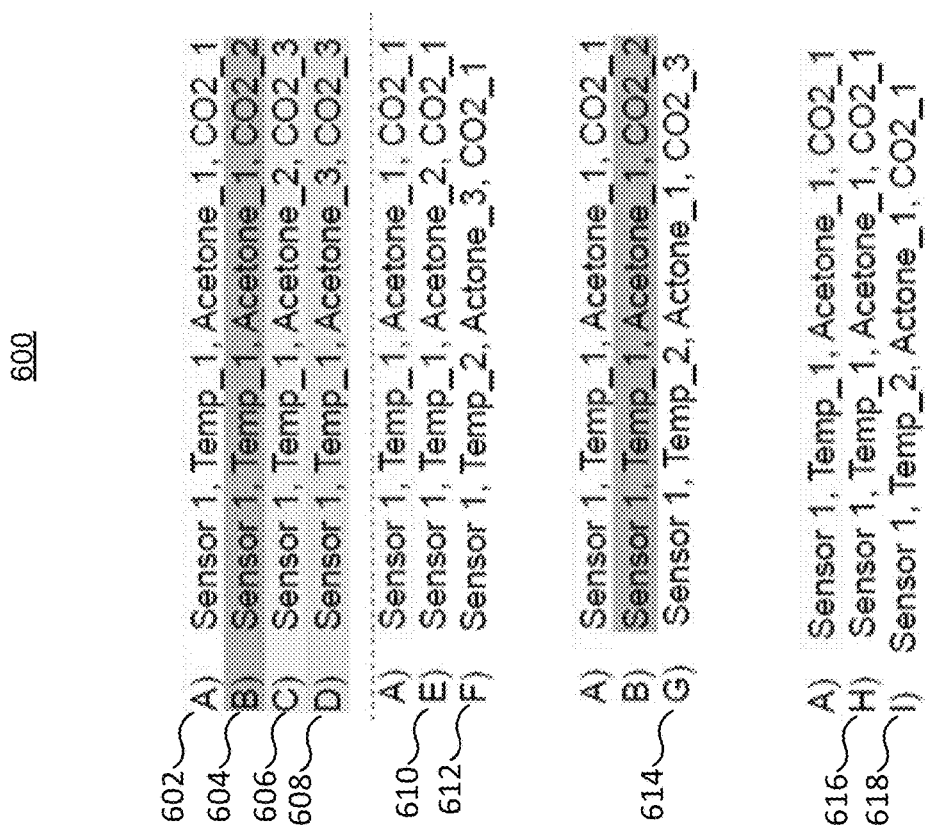
FIG. 6 is a diagram illustrating an exemplary method that may be performed in some embodiments may operate.

The training module 104 of the system 100 may perform functionality as illustrated in FIGS. 3, 5 and 6.

The sensor module 106 of the system 100 may perform functionality illustrated in FIGS. 2A, 2B and 3-5.

The output module 108 of the system 100 may perform functionality illustrated in FIGS. 2A, 2B and 3-5.

The machine learning module 110 of the system 100 may perform functionality as illustrated in FIGS. 2A, 2B and 3-6.

The user interface module 116 of the system 100 may display information based on functionality as illustrated in FIGS. 2A, 2B and 3-6.

While the databases 120, 122 and 124 are displayed separately, the databases and information maintained in a database may be combined together or further separated in a manner that promotes retrieval and storage efficiency and/or data security.

Figure 2A:
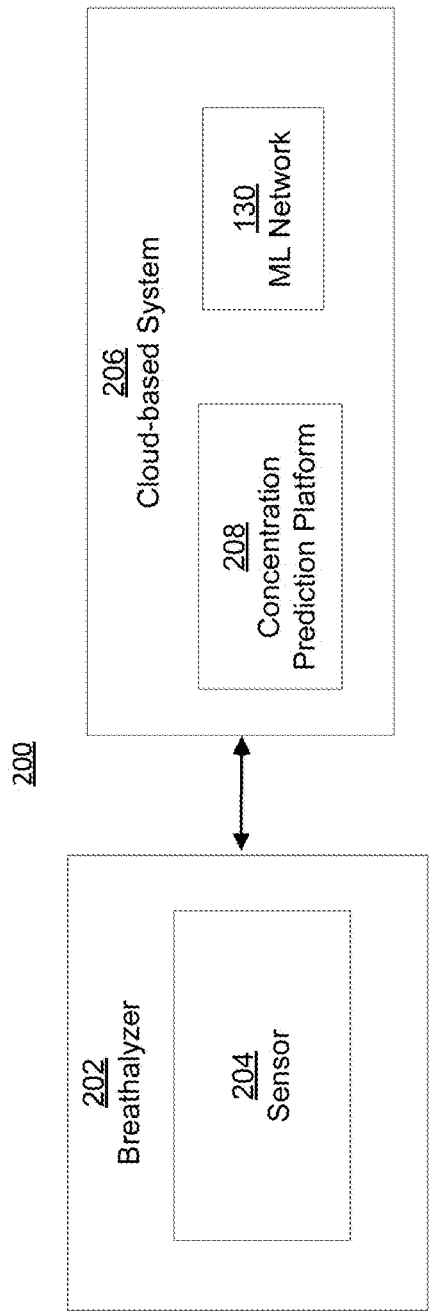
FIG. 2A is a diagram illustrating an exemplary environment in which some embodiments may operate.

As shown in FIG. 2A, diagram 200 illustrates an exemplary environment in which some embodiments may operate. A breathalyzer component 202 for operation of an end user may include a sensor 204. The breathalyzer component 202 may include a plurality of sensors. For example, the sensor(s) 204 may be an electro-chemical cell. The end user may provide one or more samples of their exhaled breath into the breathalyzer component 202. The sensor 204 may be exposed to one or more of exhaled breath samples. The sensor 204 generates data based on the one or more of exhaled breath samples that comes into contact with the sensor 204. The sensor 204 sends the data a cloud-based computing system 206. For example, the cloud-based computing system 206 may include (or host) the Concentration Prediction Platform 208 which may further include access to a respective machine learning network 130 for each sensor at the breathalyzer component 202. It is understood that the machine learning network 130 and/or the cloud-based computing system 206 may be part of the Concentration Prediction Platform 208. Various embodiments may provide for the machine learning network 130 situated internal to or external to the cloud-based computing system 206.

The Concentration Prediction Platform 208 may send a signal from the sensor 204 to a machine learning network 130 trained specifically for that sensor 204 and receive output from the machine learning network 130. According to various embodiments, the output may be an algorithm(s) identified to be applied to the sensor 204. For example, the identified algorithm may update one or more capabilities of the sensor 204 and/or improve a current performance status or health of the sensor 204. According to various embodiments, the output may be a concentration of acetone and a concentration of carbon dioxide present in the one or more of exhaled breath samples upon which the sensor's 204 signal is based.

Figure 2B:
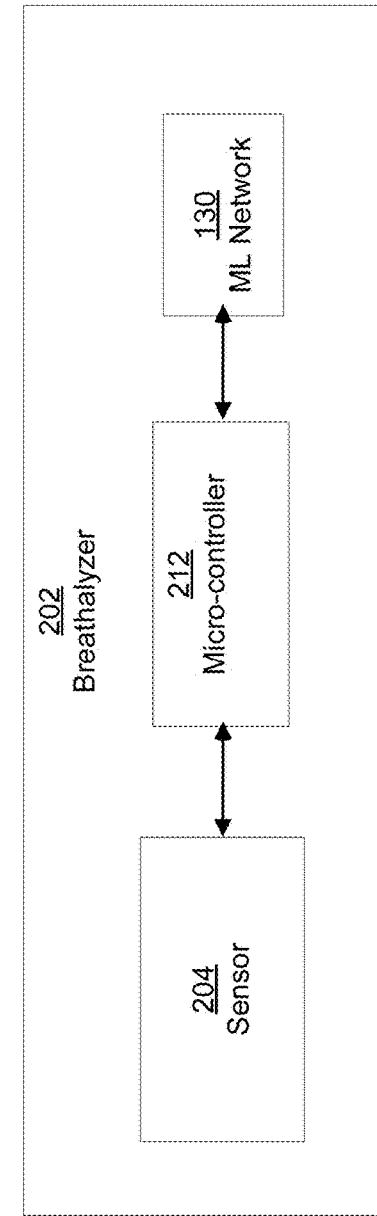
FIG. 2B is a diagram illustrating an exemplary environment in which some embodiments may operate.

As shown in diagram 210 od FIG. 2B, machine learning network 130 may be trained to output predictions for a particular sensor 204 and may be pre-loaded onto a device 202 that houses the particular sensor 204. A microcontroller 212 of the device 202 may access the machine learning network 130 in order to calculate and output predictions locally at the device 202. It is understood that the combination of the sensor 204, microcontroller 212 and the machine learning network 130 is an embodiment of the Concentration Prediction Platform 208 implemented within the device 202. The device 202 itself may also be considered as a part of the Concentration Prediction Platform 208—along with the sensor 204, microcontroller 212 and the machine learning network 130—according to one or more embodiments.

As shown in the diagram 300 of FIG. 3, various embodiments of the machine learning network 130 of the Concentration Prediction Platform may include one or more convolutional layers 302, a max pooling layer 304, a flattening layer 306, a dense layer 308, embedding layer 310, dense layers 312, 314 for predicting carbon dioxide and acetone levels and a concatenation layer 316. According to various embodiments, the embedding layer 310 may also be a dense layer. In other embodiment, the embedding layer 310 may have one or more characteristics of a dense layer. According to various embodiments, the machine learning network 130 may correspond to a particular sensor. As such, for a particular embodiment that includes multiple sensors, it is understood that each respective sensor may have a distinct corresponding machine learning network deployed to make predictions based on samples of exhaled breath that come in contact with that respective sensor.

To train the machine learning network 130 for a particular sensor, training nonets based on nine different tests (i.e. actual tests and/or simulated tests) are performed by the particular sensor with regard to different samples are input into the machine learning network 130. Signals from each training nonet test are input into the machine learning network 130 individually and separately. When the machine learning network 130 is deployed, the input may be a signal based on a sample of exhaled breath on the same particular sensor. The machine learning network 130 may output a predicted level of concentration of carbon dioxide 318 and a predicted level of acetone 320. It is understood that, in various embodiments, input to the machine learning network 130 may be based on a signal received from a sensor where the signal is generated in response to the sensor's chemical reaction to a sample of exhaled breath.

Various embodiments of the Concentration Prediction Platform may use any suitable machine learning training techniques to train the machine learning network 130 for each sensor, including, but not limited to a neural net based algorithm, such as Artificial Neural Network, Deep Learning; a robust linear regression algorithm, such as Random Sample Consensus, Huber Regression, or Theil-Sen Estimator; a kernel based approach like a Support Vector Machine and Kernel Ridge Regression; a tree-based algorithm, such as Classification and Regression Tree, Random Forest, Extra Tree, Gradient Boost Machine, or Alternating Model Tree; Naïve Bayes Classifier; and other suitable machine learning algorithms.

As shown in the flowchart 400 of FIG. 4, at step 402, the Concentration Prediction Platform receives sensor data associated with exhaled breath. For example, the received sensor data may be a signal. In various embodiments, the Concentration Prediction Platform receives at least one sample of exhaled breath at an electro-chemical cell(s). The electro-chemical cell oxidizes and reduces the sample of exhaled breath to create an electric current that corresponds to the sample of exhaled breath. The electro-chemical cell converts the electric current into a voltage signal. The electro-chemical cell utilizes the voltage to capture time series data based on the sample of exhaled breath. The electro-chemical cell sends the time series data to the Concentration Prediction Platform and the Concentration Prediction Platform receives the time series data.

In various embodiments, the sensor may be an electrolyte sensor that is reactive to acetone. The electrolyte sensor may include a substrate based on potassium hydroxide or sodium hydroxide. A surface of the electrolyte sensor may be platinum black. The electrolyte sensor oxidizes acetone present in a sample(s) of exhaled breath and reduces carbon dioxide present in the sample(s) of exhaled breath to carbon monoxide. In response to being exposed to the sample(s) of exhaled breath, the electrolyte sensor outputs time series data based on a combination signal representative of the acetone and the carbon dioxide present in the sample(s) of exhaled breath. In various embodiments, sensor data may be based on extraction of the concentrations of acetone and/or carbon dioxide from the sensor signal and/or sensor metadata related to the instrument and/or environmental conditions under which the sample was taken. In other embodiments, the sensor metadata may also include numerical descriptors of features of the signal, such as peak height(s). In other embodiments, the machine learning network may also utilize the interaction of the signal from the sensor with other signals (real and/or simulated).

At step 404, the Concentration Prediction Platform utilizes at least a portion of the sensor data as input to a machine learning network. According to various embodiments, the Concentration Prediction Platform analyzes the received sensor data (e.g. signal) according to a cross-point observation in the machine learning network. The cross-point observation may represent by a response curve location, through which any acetone response curve will intersect, for a particular amount of acetone concentration at a particular temperature regardless of any variable amount of carbon dioxide concentration. Various aspects of the cross-point observation are further described herein at least with regard to FIG. 5.

At step 406, the Concentration Prediction Platform receives output from the machine learning network based in part on a concentration of acetone and a concentration of carbon dioxide present in the exhaled breath. For example, the machine learning network determines a status of the electro-chemical cell and the Concentration Prediction Platform receives output from the machine learning network identifying one or more algorithms to be applied to the electro-chemical cell. According to various embodiments, the Concentration Prediction Platform receives output from the machine learning network indicating whether an individual that provided the exhaled breath is experiencing an extent of weight loss due primarily to burning fat or loss of water weight.

According to various embodiments, the machine learning network may be trained to detect other substances (e.g. hydrogen, ethanol, methane) in exhaled breath samples that may be suspected as interfering with accurately measuring acetone concentration and/or carbon dioxide concentration. The machine learning network may predict the concentration of the other substances and determine acetone concentration levels and/or carbon dioxide concentration levels that account for (i.e. corrects for) an extent of interference from the other substances present in exhaled breath samples. According to various embodiments, the machine learning network may be trained to determine a concentration of ethanol, isopropanol, methanol, methane, hydrogen and/or acetaldehyde in place of a concentration(s) of acetone.

As shown in the flowchart 500 of FIG. 5, at step 502, the Concentration Prediction Platform trains a machine learning network according to a cross-point observation. At step 504, the Concentration Prediction Platform defines the cross-point observation at least in part as an intersection of a first acetone response curve and a second acetone response curves with respect to the same sensor. In various embodiments, defining the cross-point observation may occur during training of the machine learning network. It is understood that embodiments described herein are not limited to two acetone response curves for the same sensor and that a respective response curve represents a rate of a chemical reaction at a particular sensor at a given temperature with respect to present acetone and carbon dioxide concentrations.

According to various embodiments, input data for training the machine learning model may be based on an underlying scientific observation that a particular sensor's response curves for a fixed concentration of acetone at a fixed temperature will intersect at a given response curve point regardless of variable concentrations of carbon dioxide. Input training data is formatted to assume the presence of such cross-points across all response curves for a particular sensor with respect to fixed acetone concentration(s) at fixed temperature(s) at variable carbon dioxide concentrations. There may be multiple, differing fixed acetone concentrations at a fixed temperature amount associated with multiple response curves that have their own shared intersection point regardless of the carbon dioxide concentration. Stated differently, all response curves for a chemical reaction at a particular sensor—for a fixed acetone concentration and fixed temperature but variable carbon dioxide concentrations—will show a same conversion rate at some point in time. As such, an invariant point will be shared across all the response curves representing signals from the same sensor that has come into contact with different samples that include the same fixed acetone concentration at the same fixed temperature regardless of whether those samples include varying concentration levels of carbon dioxide. According to various embodiments, the cross-point observation may further be defined as response curves intersecting at a same point with respect to samples that include a fixed concentration of acetone, a fixed concentration of carbon dioxide but varying temperatures.

According to the cross-point observation, a first acetone response curve may be based on a sample of the exhaled breath that presents a first amount of acetone concentration (a1) at a first temperature (t1) with first amount of carbon dioxide concentration (co1) and a second acetone response curve is based on a different sample of exhaled breath that presents the same first amount of acetone concentration (a1) at the same first temperature (t1) with a second amount of carbon dioxide concentration (co2), the first amount of carbon dioxide concentration (co1) differing from the second amount of carbon dioxide concentration (co2). It follows then that a third acetone response curve associated with the same first amount of acetone concentration (a1) at the same first temperature (t1) with a third amount of carbon dioxide concentration (co3) will intersect with the first response curve at the same point where the first and second response curves intersect.

FIG. 6 shows a diagram 600 of a subset of an exemplary training data for various embodiments as described herein. The training data includes a plurality of training subsets, or training nonets. Each training nonet may be a single unit of training data that includes results from nine separate sensor tests. That is, a training nonet may represent nine different tests on varying samples performed by the same sensor. As shown in diagram 600 of an exemplary training nonet, each test 602, 604, 606, 608, 610, 612, 614, 616, 618 may have quadruplet values representing sensor results from the same sensor for acetone, temperature and carbon dioxide that reflect the cross-point observation. Four tests 602, 604, 606, 608 create a first set of tests in the training nonet that represents a contrastive loss set. For example, the Test A 602 represents an anchor model for a first sensor and a first acetone concentration, a first carbon dioxide concentration and a first temperature. Test B 604 and Test C 606 represent positive and negative models, respectively, of the Test A 602 anchor model. Test B 604 differs from Test A 602 only by a different carbon dioxide concentration. Test C 606 differs from Test A 602 by different acetone and carbon dioxide concentrations. Test D 608 represents an anchor model for carbon dioxide, whereby Test C 606 is its positive model by way of only a different acetone concentration. Test B 604 is the negative model of Test D 608 due to different acetone carbon dioxide concentrations. A second set of tests 602, 610, 612 in the training nonet may be based on a fixed carbon dioxide concentration level, with varying temperatures and varying acetone concentration levels. A third set of tests 602, 604, 614 in the training nonet may be based on a fixed acetone concentration level, with varying temperatures and carbon dioxide concentration levels. A fourth set of tests 602, 616, 618 in the training nonet may be based on different temperatures with a fixed acetone and carbon dioxide concentration levels. Test A 602 and Test H 616 may be different underlying sensor tests.

According to various embodiments, training the machine learning network of the Concentration Prediction Platform may include generating simulated training data. The Concentration Prediction Platform obtains quadruplet values from a plurality of actual sensor tests and generates simulated sensor test results based on averages of the actual sensor tests. For example, generating simulated sensor test results may include a random selection of actual sensor tests with different carbon dioxide concentration levels and generating simulated quadruplet values based on the averages of the quadruplet values from the randomly selected actual sensor tests. It is understood that random selection of actual sensor tests need not be based solely on differing carbon dioxide concentration levels. Random selection may also be based on differing acetone concentration levels and/or differing temperatures. The training data corpus may therefore include both actual sensor tests and simulated sensor tests. A training nonet may have any ratio between actual and simulated sensor tests.

According to various embodiments, to train a machine learning model, the training data may be input nonets whereby each of the nine distinct tests of a training nonet will be represented as a signal and will individually pass through the machine learning model for a particular sensor. For example, nine signals may correspond to a training nonet's nine tests 602, 604, 606, 608, 610, 612, 614, 616, 618, respectively. Each signal may separately and individually be input into the machine learning model. For example, the machine learning model for a particular sensor may be based on machine learning network 130 as illustrated in FIG. 3. According to various embodiments, training nonets may also be based on a concentration(s) of ethanol, isopropanol, methanol, methane, hydrogen or acetaldehyde in place of a concentration(s) of acetone.

Figure 7:
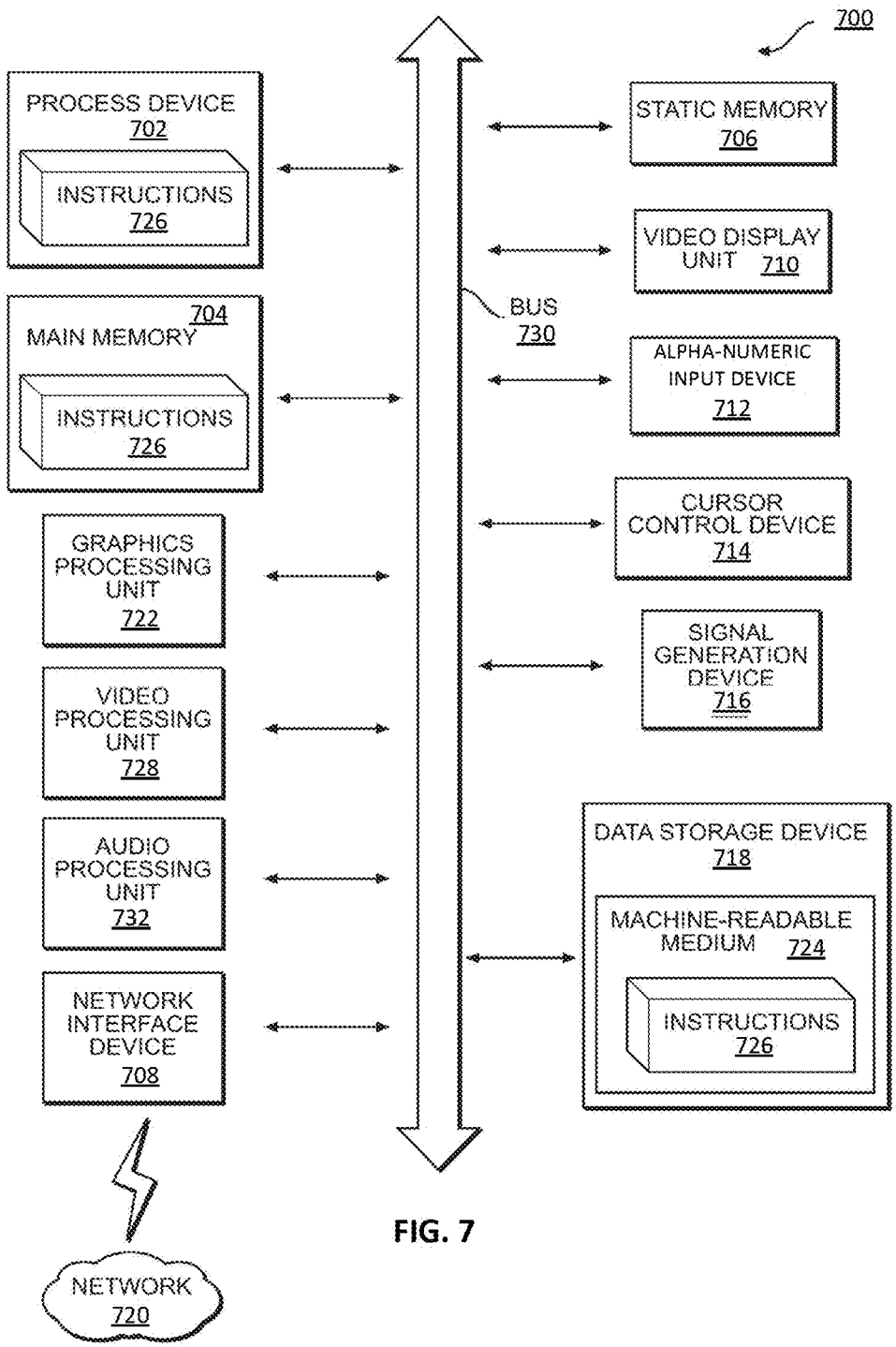
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716

(e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
   receiving sensor data associated with at least one sensor;
   utilizing at least a portion of the sensor data of a respective sensor as input to a machine learning network trained at least on a cross-point observation indicating a response curve location at which response curves at the respective sensor intersect, the response curves corresponding to exposure of the respective sensor to multiple training samples of a same amount of an analyte concentration at a same particular temperature, wherein a variable amount of carbon dioxide concentrations are present across the multiple training samples; and
   receiving output from the machine learning network based in part on exposure of the at least one sensor to a present sample having a given concentration of the analyte and a given concentration carbon dioxide.

2. The computer-implemented method of claim 1, wherein the analyte comprises one of:
   ethanol, isopropanol, methanol, methane, hydrogen or acetaldehyde.

3. The computer-implemented method of claim 1, wherein receiving sensor data comprises:
   receiving at least one sample of exhaled breath at one or more electro-chemical cells that performs at least one of oxidization and reduction of the sample of exhaled breath to create a current that corresponds to the sample of exhaled breath;

converting the current into a voltage signal; and
utilizing the voltage of the signal to capture time series data based on the sample of exhaled breath.

4. The computer-implemented method of claim 3, wherein receiving sensor data comprises one of:
receiving the time series data at a microcontroller, the machine learning network accessible by the microcontroller.

5. The computer-implemented method of claim 1, further comprising:
wherein the analyte comprises one of: ethanol, isopropanol, methanol, methane, hydrogen or acetaldehyde;
defining the cross-point observation based at least in part as an intersection of a first analyte response curve and a second analyte response curve;
(i) wherein the first analyte response curve at a given sensor is based on a first test sample that presents a first amount of analyte concentration at a first temperature with first amount of carbon dioxide concentration; and
(ii) wherein the second analyte response curve at the same given sensor is based on a different second test sample that presents the same first amount of analyte concentration at the same first temperature with a second amount of carbon dioxide concentration, the first amount of carbon dioxide concentration differing from the second amount of carbon dioxide concentration.

6. The computer-implemented method of claim 1, wherein receiving output from the machine learning network comprises:
wherein the present sample comprises exhaled breath;
determining a status of the electro-chemical cell via the machine learning network; and
receiving output identifying one or more algorithms to be applied to the electro-chemical cell to modify the status of the electro-chemical cell.

7. The computer-implemented method of claim 1, wherein receiving output from the machine learning network comprises:
wherein the present sample comprises exhaled breath;
receiving an indication whether an individual that provided the exhaled breath is experiencing an extent of weight loss due primarily to one of: burning of fat and loss of water weight.

8. A system comprising one or more processors, and a non-transitory computer-readable medium including one or more sequences of instructions that, when executed by the one or more processors, cause the system to perform operations comprising:
receiving sensor data associated with at least one sensor exposed to exhaled breath;
utilizing at least a portion of the sensor data of a respective sensor as input to a machine learning network trained at least on a cross-point observation indicating a response curve location at which response curves at the respective sensor intersect, the response curves corresponding to exposure of the respective sensor to multiple training samples of a same amount of analyte concentration at a same particular temperature, wherein a variable amount of carbon dioxide concentrations are present across the multiple training samples; and
receiving output from the machine learning network based in part on a concentration of analyte and a concentration carbon dioxide present in the exhaled breath.

9. The system of claim 8, wherein the analyte comprises one of:
ethanol, isopropanol, methanol, methane, hydrogen or acetaldehyde.

10. The system of claim 8, wherein receiving sensor data associated with exhaled breath comprises:
receiving at least one sample of exhaled breath at one or more electro-chemical cells that performs at least one of oxidization and reduction of the sample of exhaled breath to create a current that corresponds to the sample of exhaled breath;
converting the current into a voltage signal; and
utilizing the voltage of the signal to capture time series data based on the sample of exhaled breath.

11. The system of claim 10, wherein receiving sensor data associated with exhaled breath comprises:
receiving the time series data at a microcontroller, the machine learning network accessible by the microcontroller.

12. The system of claim 8, further comprising:
wherein the analyte comprises one of: ethanol, isopropanol, methanol, methane, hydrogen or acetaldehyde;
defining the cross-point observation based at least in part as an intersection of a first analyte response curve and a second analyte response curve;
(i) wherein the first analyte response curve at a given sensor is based on a first test sample that presents a first amount of analyte concentration at a first temperature with first amount of carbon dioxide concentration; and
(ii) wherein the second analyte response curve at the same given sensor is based on a different second test sample that presents the same first amount of analyte concentration at the same first temperature with a second amount of carbon dioxide concentration, the first amount of carbon dioxide concentration differing from the second amount of carbon dioxide concentration.

13. The system of claim 8, wherein receiving output from the machine learning network based in part on a concentration of analyte and a concentration carbon dioxide present in the exhaled breath comprises:
determining a status of the electro-chemical cell via the machine learning network; and
receiving output identifying one or more algorithms to be applied to the electro-chemical cell to modify the status of the electro-chemical cell.

14. The system of claim 8, wherein receiving output from the machine learning network based in part on a concentration of analyte and a concentration carbon dioxide present in the exhaled breath comprises:
receiving an indication whether an individual that provided the exhaled breath is experiencing an extent of weight loss due primarily to one of: burning of fat and loss of water weight.

15. A computer program product comprising a non-transitory computer-readable medium having a computer-readable program code embodied therein to be executed by one or more processors, the program code including instructions to:
receiving sensor data associated with at least one sensor exposed to exhaled breath;
utilizing at least a portion of the sensor data of a respective sensor as input to a machine learning network trained at least on a cross-point observation indicating a response curve location at which response curves at the respective sensor intersect, the response curves corresponding to exposure of the respective sensor to multiple training samples of a same amount of analyte concentration at a same particular temperature, wherein a variable amount of carbon dioxide concentrations are present across the multiple training samples; and receiving output from the machine learning network based in part on a concentration of analyte and a concentration carbon dioxide present in the exhaled breath.

16. The computer program product of claim 15, wherein the analyte comprises one of:

ethanol, isopropanol, methanol, methane, hydrogen or acetaldehyde.

17. The computer program product of claim 15, wherein receiving sensor data associated with exhaled breath comprises:

receiving at least one sample of exhaled breath at one or more electro-chemical cells that performs at least one of oxidization and reduction of the sample of exhaled breath to create a current that corresponds to the sample of exhaled breath;

converting the current into a voltage signal; and utilizing the voltage of the signal to capture time series data based on the sample of exhaled breath.

18. The computer program product of claim 17, wherein receiving sensor data associated with exhaled breath comprises:

receiving the time series data at a microcontroller, the machine learning network accessible by the microcontroller.

19. The computer program product of claim 15, further comprising:

wherein the analyte comprises one of: ethanol, isopropanol, methanol, methane, hydrogen or acetaldehyde;

defining the cross-point observation based at least in part as an intersection of a first analyte response curve and a second analyte response curve;

(i) wherein the first analyte response curve at a given sensor is based on a first test sample that presents a first amount of analyte concentration at a first temperature with first amount of carbon dioxide concentration; and (ii) wherein the second analyte response curve at the same given sensor is based on a different second test sample that presents the same first amount of analyte concentration at the same first temperature with a second amount of carbon dioxide concentration, the first amount of carbon dioxide concentration differing from the second amount of carbon dioxide concentration.

20. The computer program product of claim 15, wherein receiving output from the machine learning network based in part on a concentration of analyte and a concentration carbon dioxide present in the exhaled breath comprises:

determining a status of the electro-chemical cell via the machine learning network; and receiving output identifying one or more algorithms to be applied to the electro-chemical cell to modify the status of the electro-chemical cell.

\* \* \* \* \*